(12) United States Patent
Lee et al.

(10) Patent No.: US 11,819,306 B2
(45) Date of Patent: Nov. 21, 2023

(54) HELMET AND METHOD OF CONTROLLING THE SAME

(71) Applicants: Hyundai Motor Company, Seoul (KR); Kia Motors Corporation, Seoul (KR)

(72) Inventors: Jeong-Eom Lee, Yongin-si (KR); Youngmin Park, Seoul (KR); Seona Kim, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 282 days.

(21) Appl. No.: 17/108,255

(22) Filed: Dec. 1, 2020

(65) Prior Publication Data

US 2021/0330017 A1 Oct. 28, 2021

(30) Foreign Application Priority Data

Apr. 22, 2020 (KR) ........................ 10-2020-0048615

(51) Int. Cl.
| | |
|---|---|
| *A61B 5/00* | (2006.01) |
| *G10L 25/63* | (2013.01) |
| *G06V 20/10* | (2022.01) |
| *G06V 40/16* | (2022.01) |
| *H04W 4/90* | (2018.01) |

(52) U.S. Cl.
CPC .......... *A61B 5/0006* (2013.01); *A61B 5/6803* (2013.01); *G06V 20/10* (2022.01); *G06V 40/174* (2022.01); *G10L 25/63* (2013.01); *H04W 4/90* (2018.02)

(58) Field of Classification Search
CPC ........................... A61B 5/6803; A61B 5/0006
See application file for complete search history.

(56) References Cited

U.S. PATENT DOCUMENTS

| | | | |
|---|---|---|---|
| 2009/0082692 A1* | 3/2009 | Hale | A61B 5/16 600/301 |
| 2014/0173812 A1* | 6/2014 | Krueger | A41D 13/0155 2/455 |
| 2018/0213873 A1* | 8/2018 | Brice | A42B 3/046 |
| 2019/0167095 A1* | 6/2019 | Krueger | A61B 3/113 |

* cited by examiner

*Primary Examiner* — Benyam Haile
(74) *Attorney, Agent, or Firm* — MORGAN, LEWIS & BOCKIUS LLP

(57) ABSTRACT

A helmet configured for improving the safety of a user of a personal mobility by measuring an electroencephalogram (EEG) of the user using an EEG detector provided in a helmet, determining an accident situation based on the measured EEG, and operating a safety device is provided. The helmet includes a body configured to form an exterior of the helmet and can be worn on a user's head; the EEG detector provided on the body and configured to detect EEG of the user; and a controller configured to determine an accident-related situation based on an EEG signal output from the EEG detector, and to generate a control signal for operating a safety device according to the determined accident-related situation.

18 Claims, 9 Drawing Sheets

HELMET AND METHOD OF CONTROLLING THE SAME

CROSS-REFERENCE TO RELATED APPLICATION(S)

The present application claims priority to Korean Patent Application No. 10-2020-0048615, filed on Apr. 22, 2020, the entire contents of which is incorporated herein for all purposes by this reference.

BACKGROUND OF THE INVENTION

Field of the Invention

The present invention relates to a helmet for protecting a user's head of a personal mobility, and a method of controlling the same.

Description of Related art

As environmental regulations are strengthened and traffic congestion increases due to an increase in traffic volume, the use of personal mobility is increasing, which can reduce traffic congestion and parking issues while minimizing the emission of environmental pollutants.

The personal mobility is a small mobile device such as a motorcycle, a bicycle, and a kickboard. Recently, products that use electricity as a power source or hybrid products that use both electricity and fuel are being released.

When moving using the personal mobility, accidents may occur due to collisions with other objects or slipping of wheels. Unlike a general vehicle, in the personal mobility, since a user is exposed to the outside, a degree of injury may be more serious when an accident occurs.

Therefore, the user of the personal mobility is required to wear a protective device that can protect the user, such as a helmet.

The information included in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing a helmet configured for improving the safety of a user of a personal mobility by measuring an electroencephalogram (EEG) of the user using an EEG detector provided in a helmet, determining an accident situation based on the measured EEG, and operating a safety device, and a method of controlling the helmet.

Additional aspects of the present invention will be set forth in part in the description which follows, and in part, will be obvious from the description, or may be learned by practice of the present invention.

In accordance with an aspect of the present invention, a helmet may include a body configured to form an exterior of the helmet and can be worn on a user's head; an electroencephalogram (EEG) detector provided on the body and configured to detect EEG of the user; and a controller configured to determine an accident-related situation based on an EEG signal output from the EEG detector, and to generate a control signal for operating a safety device according to the determined accident-related situation.

The controller may be configured to determine the accident-related situation by comparing a pattern of the EEG signal output from the EEG detector with a normal pattern.

The normal pattern may include a pattern of the user's EEG signal appearing in a situation not related to an accident.

The controller may be configured to compare the pattern of the EEG signal output from the EEG detector with the normal pattern to determine a current situation as at least one of the normal situation, an accident situation, and a pre-accident situation.

Based on the current situation being the accident situation or the pre-accident situation, the controller may be configured to generate the control signal for operating the safety device.

The safety device may include a wearable airbag device.

The helmet may further include a communicator connected to the controller and configured to transmit the control signal to the safety device for operating the safety device.

The helmet may further include a first camera configured to capture an image of the user; and a microphone configured to receive a speech of the user.

The controller may be configured to generate the control signal for operating the safety device based on the user image captured by the first camera and the user speech received by the microphone.

The helmet may further include a second camera connected to the controller and configured to capture a surrounding image; and a display connected to the controller and configured to display the surrounding image;

In accordance with another aspect of the present invention, in a method of controlling a helmet for a user of a personal mobility. The method may include detecting the user's electroencephalogram (EEG) using an EEG detector provided in the helmet; determining an accident-related situation based on an EEG signal output from the EEG detector; and generating a control signal for operating a safety device according to the determined accident-related situation.

The determining of the accident-related situation may include determining the accident-related situation by comparing a pattern of the EEG signal output from the EEG detector with a normal pattern.

The normal pattern may include a pattern of the user's EEG signal appearing in a situation not related to an accident.

The determining of the accident-related situation may include determining a current situation as at least one of the normal situation, an accident situation, and a pre-accident situation by comparing the pattern of the EEG signal output from the EEG detector with the normal pattern.

The method may further include, based on the current situation being the accident situation or the pre-accident situation, generating the control signal for operating the safety device.

The safety device may include a wearable airbag device.

The method may further include transmitting the control signal to the safety device for operating the safety device.

The generating of the control signal for operating the safety device may include generating the control signal for operating the safety device based on an image of the user captured by a camera provided in the helmet and a speech of the user received by a microphone provided in the helmet.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
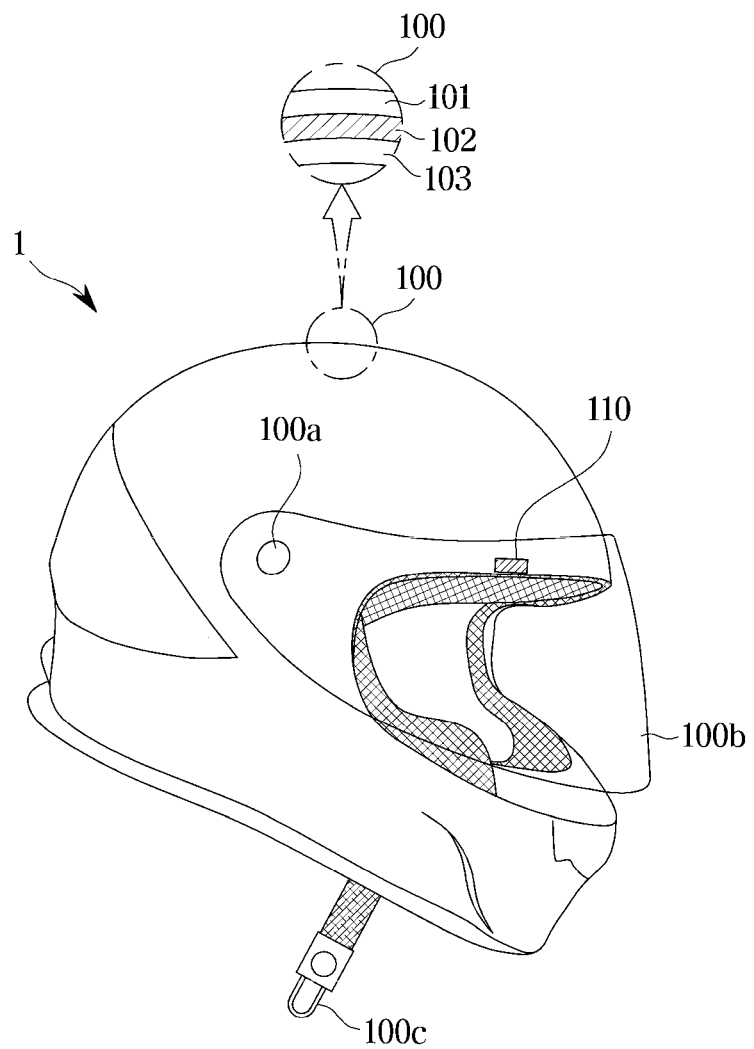
FIG. 1 is a view exemplarily illustrating an appearance of a helmet according to various exemplary embodiments of the present invention.

It may be understood that the appended drawings are not necessarily to scale, presenting a somewhat simplified representation of various features illustrative of the basic principles of the present invention. The specific design features of the present invention as included herein, including, for example, specific dimensions, orientations, locations, and shapes will be determined in part by the particularly intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the present invention(s) will be described in conjunction with exemplary embodiments of the present invention, it will be understood that the present description is not intended to limit the present invention(s) to those exemplary embodiments. On the other hand, the present invention(s) is/are intended to cover not only the exemplary embodiments of the present invention, but also various alternatives, modifications, equivalents and other embodiments, which may be included within the spirit and scope of the present invention as defined by the appended claims.

Like reference numerals refer to like elements throughout the specification. Not all elements of the embodiments of the present invention will be described, and the description of what are commonly known in the art or what overlap each other in the exemplary embodiments will be omitted. The terms as used throughout the specification, such as "~part," "~module," "~member," "~block," etc., may be implemented in software and/or hardware, and a plurality of "~parts," "~modules," "~members," or "~blocks" may be implemented in a single element, or a single "~part," "~module," "~member," or "~block" may include a plurality of elements.

It will be further understood that the term "connect" and its derivatives refer both to direct and indirect connection, and the indirect connection includes a connection over a wireless communication network.

The terms "include (or including)" and "comprise (or comprising)" are inclusive or open-ended and do not exclude additional, unrecited elements or method steps, unless otherwise mentioned. It will be further understood that the term "member" and its derivatives refer both to when a member is in contact with another member and when another member exists between the two members.

It will be understood that, although the terms first, second, third, etc., may be used herein to describe various elements, components, regions, layers and/or sections, these elements, components, regions, layers and/or sections may not be limited by these terms. These terms are only used to distinguish one element, component, region, layer or section from another region, layer or section.

It is to be understood that the singular forms "a," "an," and "the" include plural references unless the context clearly dictates otherwise.

In addition, terms such as "~part", "~group", "~block", "~member", "~module" may refer to a unit for processing at least one function or operation. For example, the terms may refer to at least one hardware processed by at least one piece of hardware such as a field-programmable gate array (FPGA)/application specific integrated circuit (ASIC), at least one software stored in a memory, or a processor.

Reference numerals used for method steps are merely used for convenience of explanation, but not to limit an order of the steps. Thus, unless the context clearly dictates otherwise, the written order may be practiced otherwise.

Hereinafter, a helmet and a method of controlling the helmet according to an aspect will be described in detail with reference to the accompanying drawings.

Figure 2:
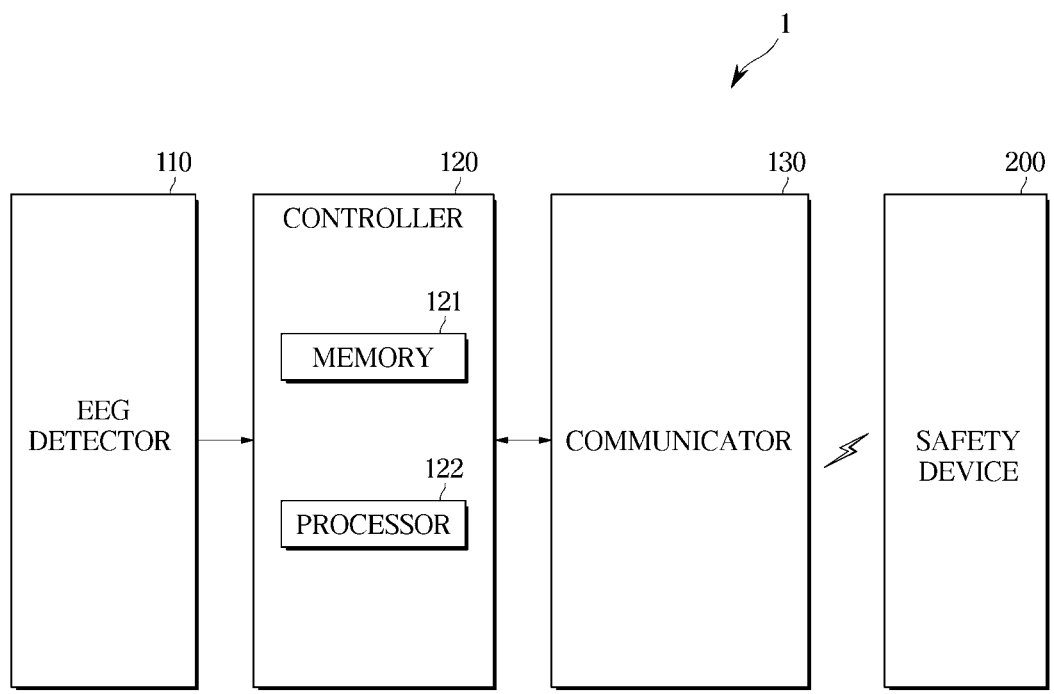
FIG. 2 is a control block diagram of a helmet according to various exemplary embodiments of the present invention.

FIG. 1 is a view exemplarily illustrating an appearance of a helmet according to various exemplary embodiments of the present invention, and FIG. 2 is a control block diagram of a helmet according to various exemplary embodiments of the present invention.

Referring to FIG. 1, a helmet 1 may include a body 100 that forms an exterior and can be worn on a user's head. The body 100 may include an external shell 101, a shock absorber 102, and an internal pad 103.

The external shell 101 may primarily absorb a shock upon collision with an object.

The shock absorber 102 may be provided between the external shell 101 and the pad 103, and secondarily absorbs shock to reduce the amount of impact transmitted to the user. The shock absorber 102 may include a styrofoam (EPS) layer which has lightweight, excellent shock absorption, ease of mold, and exhibits a stable performance regardless of whether the temperature is high or not.

The pad 103 may distribute the weight of the helmet 1 and improve the wearing sensation. That is, the pad 103 is formed of soft and elastic material.

The helmet 1 may further include a visor 100b mounted on the body 100 and movably mounted on the body 100 about an axis of a gear 100a and a fastening member 100c for fixing the body 100 to the user's head to prevent the body 100 from being separated from the user's head.

The visor 100b may protect the user's face at a time of the collision and secures the view of the user while on the move.

In order to secure the view of the user, the visor 100b may be formed of transparent material, and may include a film for glare control and UV blocking.

The fastening member 100c may be fastened or detached by the user. The fastening member 100c may be provided to come into contact with the jaw of the user and thus be formed of material having excellent hygroscopicity and durability.

Hereinafter, it will be described with reference to FIG. 1 and FIG. 2 together.

The helmet 1 may be provided in the body 100 and include an electroencephalogram (EEG) detector 110 for detecting the user's EEG and a controller 120 for determining an accident-related situation based on an EEG signal output from the EEG detector 110 and generating a control signal for operating a safety device according to the determined accident-related situation.

The EEG is a potential measured by use of an electrode to obtain a signal on a surface of a brain resulting from the synthesis of electrical signals generated by the cranial nerves. A supplementary eye field (SEF) of the brain is an area which is activated when a quick response to environmental changes is required, and there is a difference between the EEG generated from SEF in a general situation and the EEG generated from SEF in the accident-related situation. Accordingly, the helmet 1 may utilize the user's brain waves in determining the accident-related situation.

The EEG detector 110 may be mounted inside the body 100 to be in contact with the user's head. For example, the EEG detector 110 may be mounted in a position configured for contacting a forehead adjacent to a frontal lobe to detect EEG generated by the SEF. Accordingly, the helmet 1 is easy to measure EEG due to the characteristics of being worn on the user's head.

The EEG signal output from the EEG detector 110 may be input to the controller 120. The controller 120 may include at least one memory 121 in which a program that performs an operation described below and various data necessary to execute the corresponding program are stored, and at least one processor 122 that executes the stored program. When a plurality of memories and processors are provided, the memories and processors may be integrated on one chip or may be physically separated.

The controller 120 may determine the accident-related situation based on the EEG signal. The accident-related situation may include an accident situation and a pre-accident situation. For example, the controller 120 may compare a pattern of the EEG signal (hereinafter referred to as a normal pattern) generated in a normal situation not related to an accident with a pattern of the EEG signal output from the EEG detector 110. When the pattern of the EEG signal output from the EEG detector 110 is included in a range of the normal pattern, the controller 120 may determine that a current situation is the normal situation.

When the pattern of the EEG signal output from the EEG detector 110 matches the normal pattern, or when the difference is within a predetermined range even if the pattern of the EEG signal does not match the normal pattern, the controller 120 may determine that the pattern of the EEG signal is included in the range of the normal pattern.

When the pattern of the EEG signal output from the EEG detector 110 is out of the range of the normal pattern, the controller 120 may determine that it is the pre-accident situation or the accident situation.

Since the normal pattern may be previously stored in the memory 121, a detailed description of the normal pattern stored in the memory 121 will be described later.

When the current situation determined by the controller 120 based on the EEG signal output from the EEG detector 110 is the pre-accident situation or the accident situation, the controller 120 may generate the control signal for operating a safety device 200.

The safety device 200 may include a wearable airbag device such as an airbag helmet and an airbag vest.

When the safety device 200 is not provided integrally with the helmet 1, the controller 120 may transmit the control signal for operating the safety device 200 through a communicator 130. For example, when the safety device 200 is the airbag helmet or the airbag vest, the control signal for deploying the airbag may be transmitted to the safety device 200 through the communicator 130.

The communicator 130 may include at least one communication module configured to communicate with an external device. For example, the communicator 130 may include at least one of a short-range communication module, a wired communication module, and a wireless communication module.

The short-range communication module may include various short range communication modules, which is configured to transmit and receive signals using a wireless communication module in a short range area, e.g., a Bluetooth module, an infrared communication module, a Radio Frequency Identification (RFID) communication module, a Wireless Local Access Network (WLAN) communication module, a NFC communications module, and a ZigBee communication module.

The wired communication module may include various wired communication module, e.g., a Local Area Network (LAN) module, a Wide Area Network (WAN) module, or a Value Added Network (VAN) module and various cable communication module, e.g., a Universal Serial Bus (USB) module, a High Definition Multimedia Interface (HDMI) module, a Digital Visual Interface (DVI) module, a recommended standard 232 (RS-232), a power line communication, or a plain old telephone service (POTS).

The wireless communication module may include wireless communication modules supporting various wireless communication methods, e.g., a Wifi module, a Wireless broadband (Wibro) module, a global System for Mobile (GSM) Communication module, a Code Division Multiple Access (CDMA) module, a Wideband Code Division Multiple Access (WCDMA) module, a Time Division Multiple Access (TDMA) module, and a Long Term Evolution (LTE) module.

In addition to the safety device 200, the communicator 130 may communicate with a personal mobility on which the user is boarding or a user's terminal to exchange information.

Figure 3:
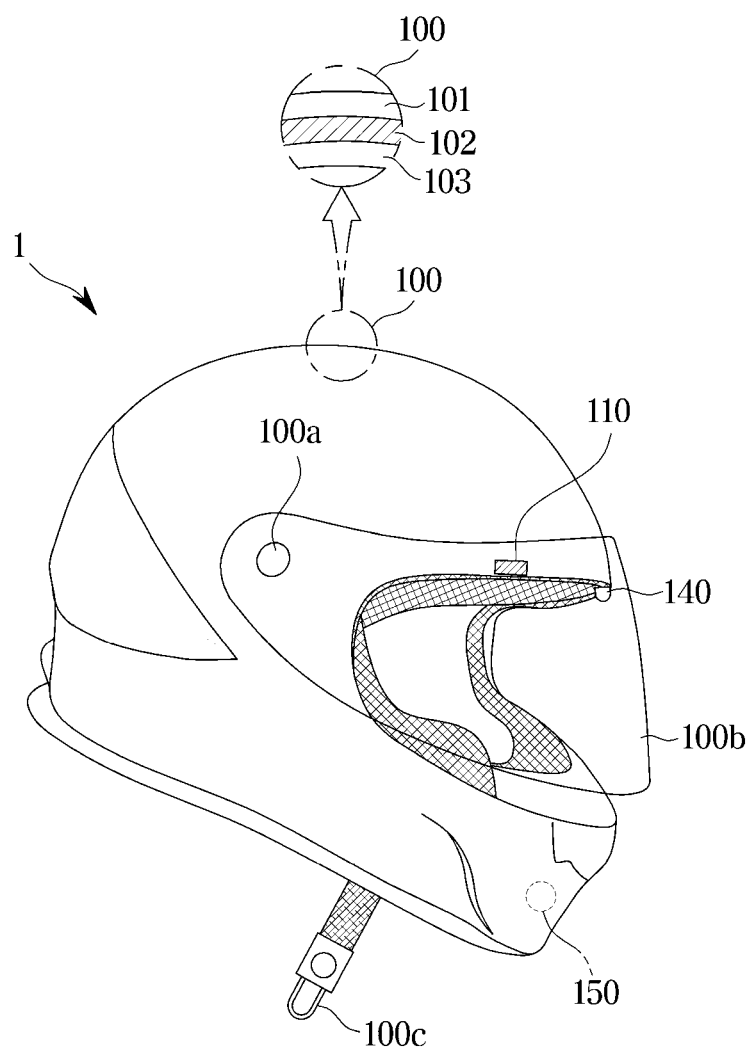
FIG. 3 is a view exemplarily illustrating an appearance of a helmet including a configuration configured for obtaining user-related information.
Figure 4:
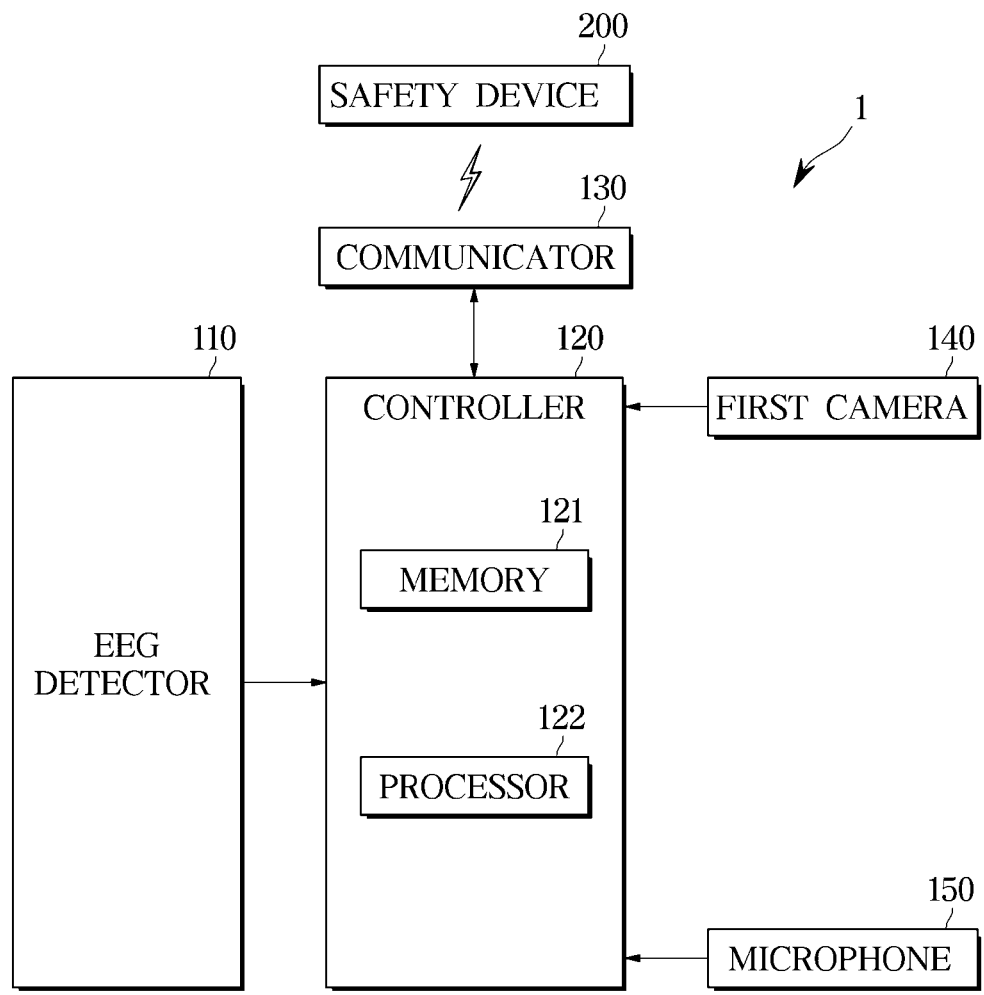
FIG. 4 is a control block diagram of the helmet illustrated in FIG. 3.

FIG. 3 is a view exemplarily illustrating an appearance of a helmet including a configuration configured for obtaining user-related information, and FIG. 4 is a control block diagram of the helmet illustrated in FIG. 3.

User-related information may include an image of the user and a speech of the user.

Referring to FIG. 3 and FIG. 4, the helmet 1 may further include a first camera 140 for capturing the user image and a microphone 150 for receiving the user speech.

The first camera 140 may be mounted in front of the body 100 and mounted to face the rear to capture the user image. The user image may include the user's face.

The microphone 150 may be mounted in front of the body 100 and mounted in a position adjacent to the user's mouth to receive the user speech.

The controller 120 may monitor the user's state based on the user image captured by the first camera 140 and the user speech received by the microphone 150.

Furthermore, the controller 120 may use at least one of the user image captured by the first camera 140 and the user speech received by the microphone 150 in generating the control signal for operating the safety device 200.

In order to improve the reliability of the operation of the safety device 200, even if the current situation determined based on the user's EEG signal corresponds to the pre-accident situation or the accident situation, the controller 120 may generate the control signal for operating the safety device 200 only when at least one of the user image and the user speech indicates the pre-accident situation or the accident situation.

For example, the controller 120 may recognize the user's expression from the user's face included in the user image, and may determine whether the user's expression indicates the pre-accident situation or the accident situation. For example, when the user's expression corresponds to an expression that appears before the accident or when the accident occurs, such as surprise or fear, the controller 120 may determine that the user's expression indicates the pre-accident situation or the accident situation.

Furthermore, the controller 120 may perform a speech recognition on the user speech to determine whether the user speech indicates the pre-accident situation or the accident situation. For example, when the user speech includes screams, exclamation, or speech related to the accident, the controller 120 may determine that the user speech indicates the pre-accident situation or the accident situation.

Alternatively, it is possible for the user to directly input an utterance for operating the safety device 200. For example, the controller 120 may generate the control signal for deploying the airbag when the user speech includes the utterance for deploying the airbag.

Figure 5:
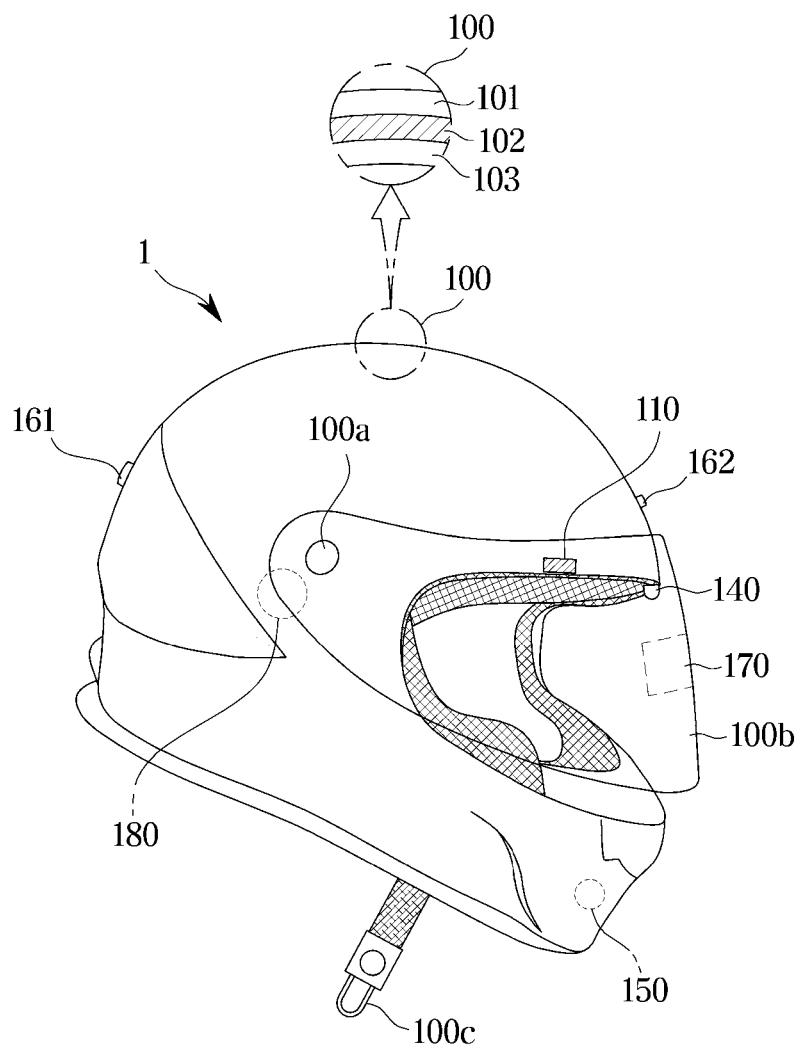
FIG. 5 is a view exemplarily illustrating an appearance of a helmet including a configuration configured for providing information about a surrounding situation to a user.
Figure 6:
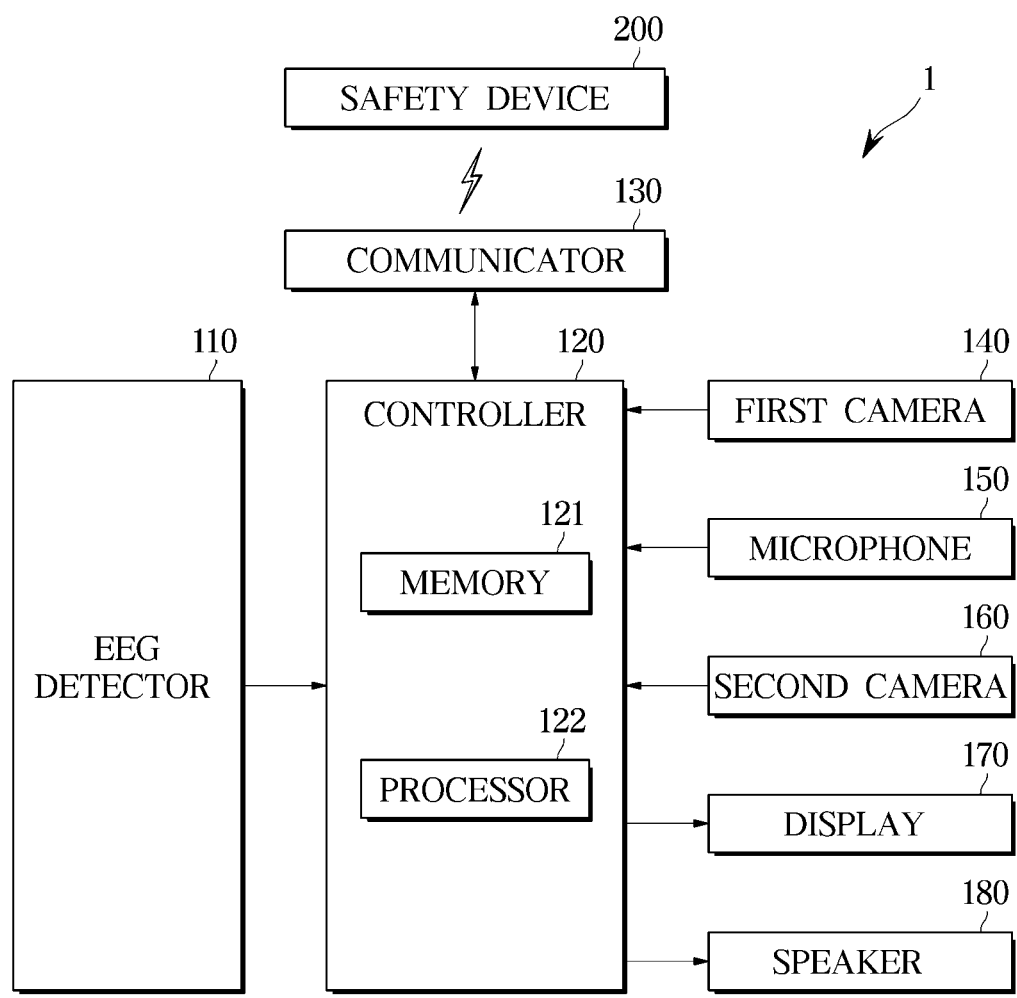
FIG. 6 is a control block diagram of the helmet illustrated in FIG. 5.

FIG. 5 is a view exemplarily illustrating an appearance of a helmet including a configuration configured for providing information about a surrounding situation to a user, and FIG. 6 is a control block diagram of the helmet illustrated in FIG. 5.

Information about the surrounding situation may include a surrounding image obtained by capturing the surroundings of the personal mobility.

Referring to FIG. 5 and FIG. 6, the helmet 1 may further include a second camera 160 for capturing the surrounding image, a display 170 for displaying the captured surrounding image, and a speaker 180 for outputting information about the surrounding situation as the speech.

The second camera 160 may include a rear camera 161 disposed toward the rear of the body 100 and a front camera 162 disposed toward the front of the body 100. The surrounding image may include a front image and a rear image, and the front image may be captured by the front camera 162 and the rear image may be captured by the rear camera 161.

Of course, left and right side images may be included in the front image and the rear image.

The display 170 may be disposed on the front of the helmet 1 so that the user can see the display 170. The display 170 may include a display panel provided on the visor 100b or may include a head up display (HUD) provided on the body 100 and projecting an image onto the visor 100b.

Furthermore, the information about the surrounding situation may include sensor information obtained by a sensor provided in personal mobility. For example, the sensor provided in the personal mobility may include at least one of a collision sensor, an acceleration sensor, and an obstacle sensor. The sensor information may include at least one of whether the personal mobility collides with an obstacle, acceleration information of the personal mobility, and obstacle information approaching around the personal mobility. The personal mobility may transmit sensor information through the communicator 130.

The surrounding image captured by the second camera 160 may be displayed on the display 170. The sensor information transmitted from the personal mobility may be displayed on the display 170 or may be output as the speech through the speaker 180.

The user may recognize the pre-accident situation or the accident situation by information about the surrounding situation provided through the display 170 or the speaker 180. However, the display 170 and the speaker 180 are merely auxiliary means for recognizing the accident-related situation, and it goes without saying that the user may recognize the accident-related situation by directly seeing, hearing, and feeling.

The pre-accident situation may be a situation before the accident occurs, and a situation in which the obstacle approaches or a situation in which the personal mobility suddenly stops may correspond to the pre-accident situation.

The accident situation may be a situation at the time of the accident or immediately after the accident, and a situation in which the obstacle and the personal mobility collide or a situation in which the personal mobility falls may correspond to the accident situation.

As described above, the memory 121 may store the normal pattern. The normal pattern may be obtained by experiment, statistics, or simulation and stored in advance, or may be obtained from the EEG signal of the user.

In the latter case, the EEG signal may be obtained every time the user wears the helmet 1, and the controller 120 may match and store the pattern of the EEG signal to the situation at the time of obtainment of the EEG signal. The controller 120 may determine the current situation based on information about the user obtained by the first camera 140 and the microphone 150 or information about the surrounding situation obtained by the second camera 160 or the sensor of the personal mobility. The current situation may include at least one of a normal situation, the pre-accident situation, and the accident situation.

The pattern of the user's EEG signal obtained in the normal situation may be stored as the normal pattern. When the pattern of the user's EEG signal obtained later is included in the range of the normal pattern, the controller 120 may determine that the current situation is the normal situation. When the pattern of the EEG signal is not included in the range of the normal pattern, the controller 120 may determine that the current situation is the accident situation or the pre-accident situation.

Furthermore, the controller 120 may match and store the pattern of the user's EEG signal obtained in the event of the pre-accident situation or the accident situation with the pre-accident situation or the accident situation. Therefore, when the pattern of the user's EEG signal obtained later corresponds to the pattern of the EEG signal matched with the pre-accident situation, the controller 120 may determine that the current situation is the pre-accident situation. When the pattern of the user's EEG signal corresponds to the pattern of the EEG signal matched with the accident situation, the controller 120 may determine that the current situation is the accident situation.

Furthermore, the controller 120 may control an operation timing of the safety device 200 differently depending on whether the current situation is the pre-accident situation or the accident situation. For example, when the current situation is the accident situation rather than the pre-accident situation, the controller 120 may rapidly control the timing of deployment of the airbag.

The obtainment of the EEG signal and matching of the obtained EEG signal with the current situation may be performed whenever the helmet 1 is used or periodically, and thus, the pattern of the EEG signal stored in the memory 121 may be updated.

Hereinafter, a method of controlling the helmet according to the exemplary embodiment will be described. In performing the method of controlling the helmet, the helmet 1 described above may be used. Therefore, the contents described with reference to FIG. 1, FIG. 2, FIG. 3, FIG. 4, FIG. 5 and FIG. 6 may be equally applied to the method of controlling the helmet even if there is no separate mention.

Figure 7:
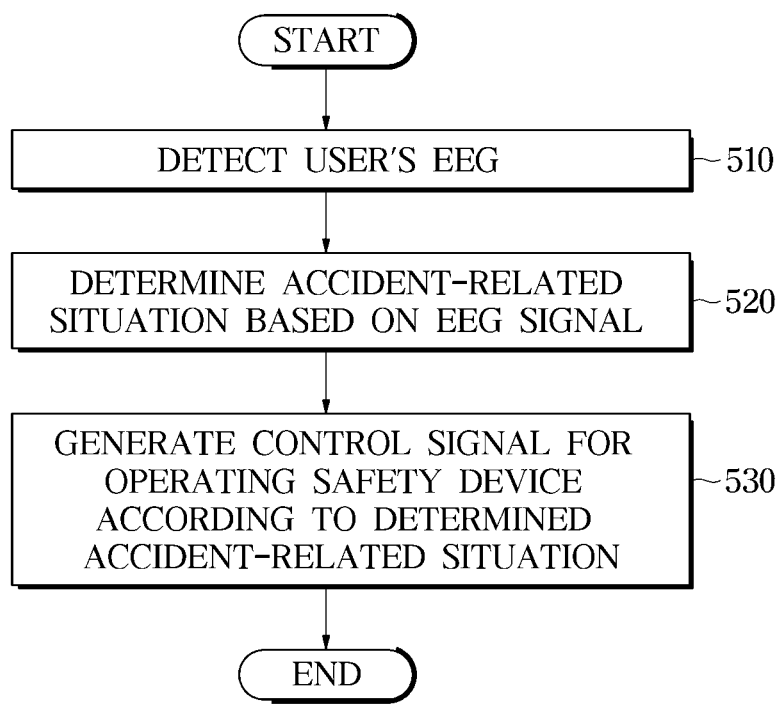
FIG. 7 is a flowchart illustrating a method of controlling a helmet according to various exemplary embodiments of the present invention.

FIG. 7 is a flowchart illustrating a method of controlling a helmet according to various exemplary embodiments of the present invention. In the exemplary embodiment of the present invention, it is assumed that the user wearing the helmet 1 has boarded personal mobility.

According to the method of controlling the helmet 1 illustrated in FIG. 7, the EEG detector 110 provided in the helmet 1 may be used to detect the user's EEG (510). A description of the EEG signal detected by the EEG detector 110 and the mounting position of the EEG detector 110 is the same as described in the exemplary embodiment of the helmet 1.

Furthermore, the accident-related situation may be determined based on the EEG signal output from the EEG detector 110 (520). The user may also recognize the surrounding situation by seeing, hearing, and feeling, and may be provided with the information about the surrounding situation from the second camera 160 provided in the helmet 1 or the sensor provided in the personal mobility. The surrounding image captured by the second camera 160 or sensor information obtained by the sensor provided in the personal mobility may be provided to the user through the display 170 or the speaker 180 provided on the helmet 1.

The accident-related situation may include at least one of the pre-accident situation and the accident situation. As described above, there is the difference between the EEG signal generated in the pre-accident situation or the accident situation and the EEG signal generated in the normal situation not related to the accident. Accordingly, the controller 120 may determine whether the current situation is the pre-accident situation or the accident situation based on the EEG signal output from the EEG detector 110.

Furthermore, the controller 120 may generate the control signal for operating the safety device 200 according to the determined accident-related situation (530). The safety device 200 may include the wearable airbag device such as the airbag helmet and the airbag vest. Accordingly, the control signal for operating the safety device 200 may include an airbag deployment signal. At the instant time, it is also possible to control the airbag deployment timing differently depending on whether the accident-related situation is the pre-accident situation or the accident situation.

Meanwhile, when the safety device 200 is not provided integrally with the helmet 1, the controller 120 may transmit the generated control signal to the safety device 200 through the communicator 130.

Figure 8:
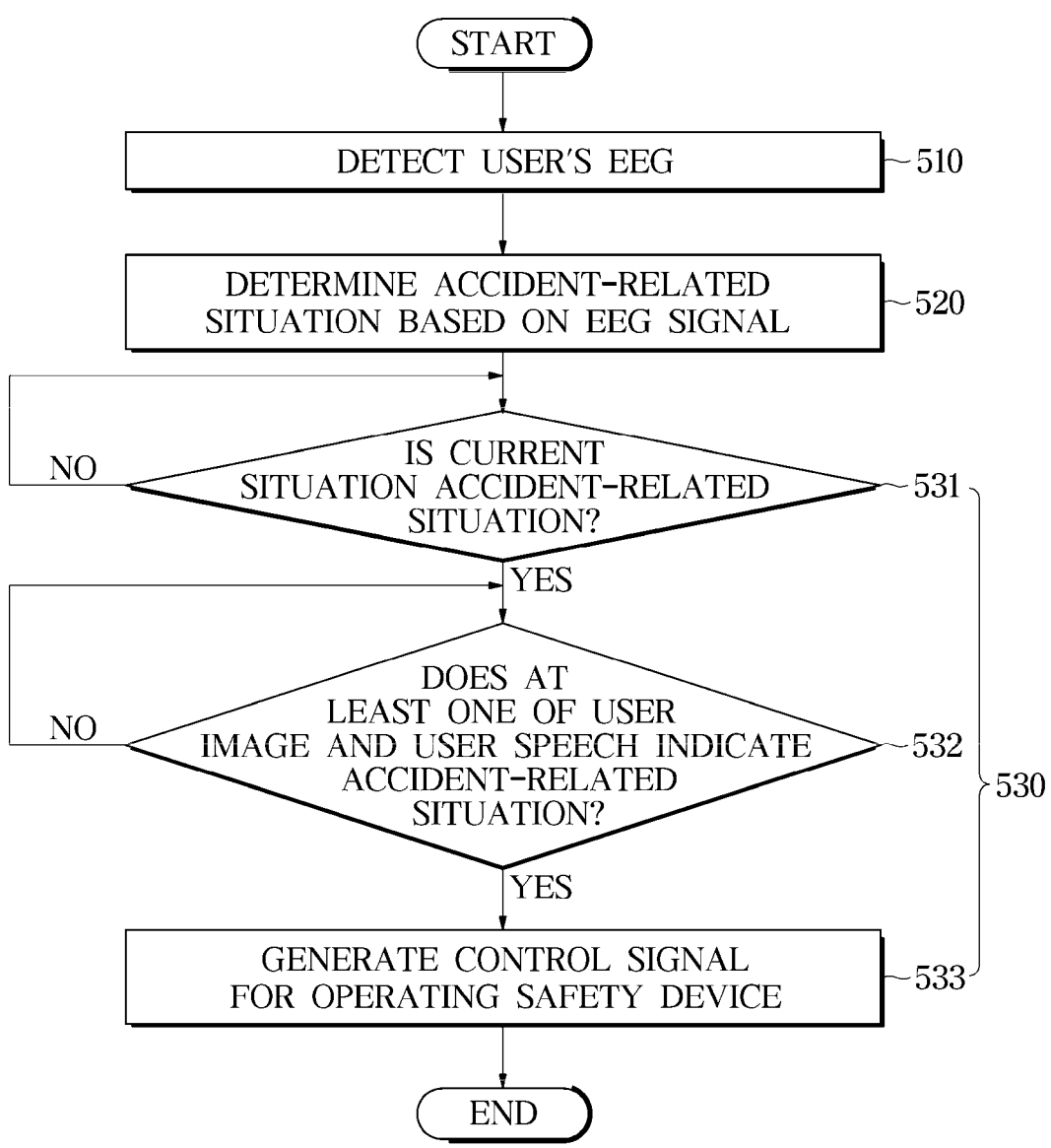
FIG. 8 is another flowchart illustrating a method of controlling a helmet according to various exemplary embodiments of the present invention.

FIG. 8 is another flowchart illustrating a method of controlling a helmet according to various exemplary embodiments of the present invention.

In the helmet control method according to the exemplary embodiment of the present invention, in order to improve the reliability of the operation of the safety device 200, even if the current situation determined based on the user's EEG signal corresponds to the pre-accident situation or the accident situation, the control signal for operating the safety device 200 may be generated only when at least one of the user image and the user speech indicates the pre-accident situation or the accident situation.

Referring to FIG. 8, generating the control signal for operating the safety device according to the determined accident-related situation 530 may include generating the control signal for operating the safety device 200 based on the user image captured by the first camera 140 provided in the helmet 1 and the user speech received by the microphone 150 provided in the helmet 1.

When it is determined that the current situation is the accident-related situation (YES in 531), or when at least one of the user image and the user speech indicates the accident-related situation (YES in 532), the controller 120 may generate the control signal for operating the safety device 200 (533).

Figure 9:
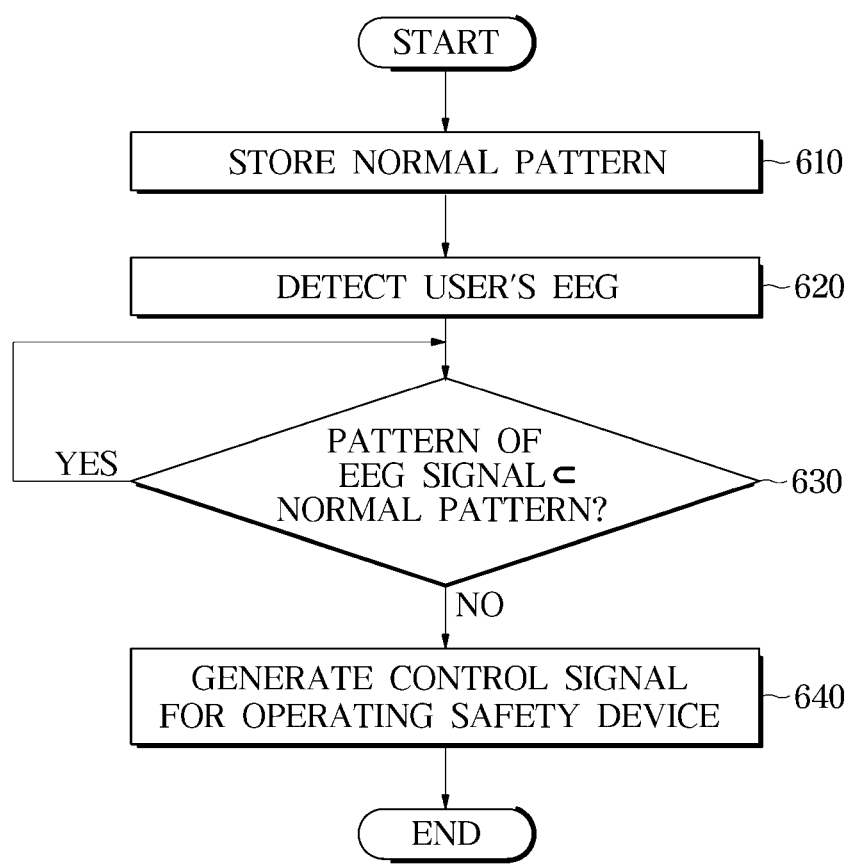
FIG. 9 is a flowchart illustrating a specific method of determining an accident-related situation based on an electroencephalogram (EEG) signal in a method of controlling a helmet according to various exemplary embodiments of the present invention.

FIG. 9 is a flowchart illustrating a specific method of determining an accident-related situation based on an electroencephalogram (EEG) signal in a method of controlling a helmet according to various exemplary embodiments of the present invention.

Referring to FIG. 9, the normal pattern of the EEG signal may be stored (610). The normal pattern may be obtained by experiment, statistics, or simulation and stored in advance, or may be obtained from the EEG signal of the user.

In the latter case, the EEG signal may be obtained every time the user wears the helmet 1, and the controller 120 may match and store the pattern of the obtained EEG signal with the current situation. The controller 120 may determine the current situation based on information about the user obtained by the first camera 140 and the microphone 150 or information about the surrounding situation obtained by the second camera 160 or the sensor of the personal mobility. The current situation may include at least one of a normal situation, the pre-accident situation, and the accident situation.

The pattern of the user's EEG signal obtained in the normal situation may be stored as the normal pattern.

The EEG signal of the user on board the personal mobility may be detected (620), and the accident-related situation may be determined by comparing the pattern of the EEG signal with the stored normal pattern. When the pattern of the EEG signal is included in the range of the normal pattern (YES in 630), the controller 120 may determine that the current situation is the normal situation.

When the pattern of the EEG signal is not included in the range of the normal pattern (NO in 630), the controller 120 may determine that the current situation is the accident-related situation and generate the control signal for operating the safety device 200 (640).

Furthermore, the controller 120 may match and store the pattern of the user's EEG signal obtained in the pre-accident situation or the accident situation with the pre-accident situation or the accident situation. Therefore, when the pattern of the user's EEG signal obtained later corresponds to the pattern of the EEG signal matched with the pre-accident situation, the controller 120 may determine that the current situation is the pre-accident situation. When the pattern of the user's EEG signal corresponds to the pattern of the EEG signal matched with the accident situation, the controller 120 may determine that the current situation is the accident situation.

According to the helmet and the method of controlling the helmet according to the embodiments, it is possible to improve the stability of the user of the personal mobility by controlling the safety device by utilizing the advantage of being able to easily detect the user's EEG due to the characteristic of the helmet worn by the user on the head and the characteristic that changes in EEG when the accident-related situation occurs.

According to the helmet and the method of controlling the helmet according to the embodiments, it is possible to improve the safety of the user of the personal mobility by measuring the EEG of the user using the EEG detector provided in the helmet, determining the accident situation based on the measured EEG, and operating the safety device.

The disclosed exemplary embodiments may be implemented in a form of a recording medium storing computer-executable instructions that are executable by a processor. The instructions may be stored in a form of a program code, and when executed by a processor, the instructions may generate a program module to perform operations of the disclosed exemplary embodiments. The recording medium may be implemented non-transitory as a computer-readable recording medium.

The non-transitory computer-readable recording medium may include all types of recording media storing commands that can be interpreted by a computer. For example, the non-transitory computer-readable recording medium may be, for example, ROM, RAM, a magnetic tape, a magnetic disc, flash memory, an optical data storage device, and the like.

For convenience in explanation and accurate definition in the appended claims, the terms "upper", "lower", "inner", "outer", "up", "down", "upwards", "downwards", "front", "rear", "back", "inside", "outside", "inwardly", "outwardly", "interior", "exterior", "internal", "external", "inner", "outer", "forwards", and "backwards" are used to describe features of the exemplary embodiments with reference to the positions of such features as displayed in the figures. It will be further understood that the term "connect" or its derivatives refer both to direct and indirect connection.

The foregoing descriptions of specific exemplary embodiments of the present invention have been presented for purposes of illustration and description. They are not intended to be exhaustive or to limit the present invention to the precise forms disclosed, and obviously many modifications and variations are possible in light of the above teachings. The exemplary embodiments were chosen and described in order to explain certain principles of the present invention and their practical application, to enable others skilled in the art to make and utilize various exemplary embodiments of the present invention, as well as various alternatives and modifications thereof. It is intended that the scope of the present invention be defined by the Claims appended hereto and their equivalents.

What is claimed is:

1. A helmet comprising:
a body provided to form an exterior of the helmet and to be wearable on a user's head;
an electroencephalogram (EEG) detector provided on the body and configured to detect EEG of the user;
a controller connected to the EEG detector and configured to determine an accident-related situation according to an EEG signal output from the EEG detector;
a first camera configured to capture a user image of the user; and
a second camera connected to the controller and configured to capture a surrounding image,
wherein the controller is configured to generate a control signal for operating a safety device according to the determined accident-related situation,
wherein the controller is configured to recognize a user's expression from a user's face included in the user image, and to determine whether the user's expression indicates the accident-related situation, and
wherein the second camera includes a rear camera disposed toward a rear of the body and a front camera disposed toward a front of the body.

2. The helmet according to claim 1, wherein the controller is configured to determine the accident-related situation by comparing a pattern of the EEG signal output from the EEG detector with a normal pattern.

3. The helmet according to claim 2, wherein the normal pattern includes a pattern of the user's EEG signal appearing in a situation not related to an accident.

4. The helmet according to claim 3, wherein the controller is configured to compare the pattern of the EEG signal output from the EEG detector with the normal pattern to determine a current situation of the user as at least one of the normal situation, an accident situation, and a pre-accident situation.

5. The helmet according to claim 4, wherein, upon determining that the current situation is the accident situation or the pre-accident situation, the controller is configured to generate the control signal for operating the safety device.

6. The helmet according to claim 5, wherein the safety device includes a wearable airbag device.

7. The helmet according to claim 6, further including:
a communicator connected to the controller and configured to transmit the control signal to the safety device for operating the safety device.

8. The helmet according to claim 1, further including:
a microphone configured to receive a speech of the user.

9. The helmet according to claim 8, wherein the controller is configured to generate the control signal for operating the safety device according to the user image captured by the first camera and the speech received by the microphone.

10. The helmet according to claim 1, further including: a display connected to the controller and configured to display the surrounding image.

11. A method of controlling a helmet for a user of a personal mobility, the method comprising:
detecting the user's electroencephalogram (EEG) using an EEG detector provided in the helmet;
determining, by a controller, an accident-related situation according to an EEG signal output from the EEG detector and information of a surrounding situation obtained by a second camera; and
generating, by the controller, a control signal for operating a safety device according to the determined accident-related situation,
wherein the generating of the control signal for operating the safety device includes:
generating the control signal for operating the safety device according to a user image of the user captured by a first camera provided in the helmet,
wherein the controller is configured to recognize a user's expression from a user's face included in the user image, and to determine whether the user's expression indicates the accident-related situation, and
wherein the second camera includes a rear camera disposed toward a rear of the body and a front camera disposed toward a front of the body.

12. The method according to claim 11, wherein the determining of the accident-related situation includes:
   determining the accident-related situation by comparing a pattern of the EEG signal output from the EEG detector with a normal pattern.

13. The method according to claim 12, wherein the normal pattern includes a pattern of the user's EEG signal appearing in a situation not related to an accident.

14. The method according to claim 13, wherein the determining of the accident-related situation includes:
   determining a current situation of the user as at least one of the normal situation, an accident situation, and a pre-accident situation by comparing the pattern of the EEG signal output from the EEG detector with the normal pattern.

15. The method according to claim 14, further including:
   upon determining that the current situation is the accident situation or the pre-accident situation, generating the control signal for operating the safety device.

16. The method according to claim 15, wherein the safety device includes a wearable airbag device.

17. The method according to claim 16, further including:
   transmitting, by the controller, the control signal to the safety device for operating the safety device.

18. The method according to claim 11, wherein the generating of the control signal for operating the safety device includes:
   generating the control signal for operating the safety device according to a speech of the user received by a microphone provided in the helmet.

\* \* \* \* \*